(12) United States Patent
Hall et al.

(10) Patent No.: US 8,280,518 B2
(45) Date of Patent: Oct. 2, 2012

(54) RECORDABLE MACROS FOR PACEMAKER FOLLOW-UP

(75) Inventors: Jeffrey A. Hall, Birmingham, AL (US);
G. Neal Kay, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1242 days.

(21) Appl. No.: 11/467,466

(22) Filed: Aug. 25, 2006

(65) Prior Publication Data

US 2006/0287692 A1 Dec. 21, 2006

Related U.S. Application Data

(62) Division of application No. 10/348,191, filed on Jan. 21, 2003, now Pat. No. 7,136,707.

(51) Int. Cl.
*A61N 1/00* (2006.01)
(52) U.S. Cl. .......... 607/59; 607/5; 607/30; 607/32; 607/60
(58) Field of Classification Search .......... 607/30–32, 607/60, 59, 5, 9
See application file for complete search history.

(56) References Cited

U.S. PATENT DOCUMENTS

| | | |
|---|---|---|
| 4,432,360 A | 2/1984 | Mumford et al. |
| 4,712,179 A | 12/1987 | Heimer |
| 4,809,697 A | 3/1989 | Causey, III et al. |
| 4,825,869 A | 5/1989 | Sasmor et al. |
| 4,928,688 A | 5/1990 | Mower |
| 5,097,831 A | 3/1992 | Lekholm |
| 5,174,289 A | 12/1992 | Cohen |
| 5,226,413 A | 7/1993 | Bennett et al. |
| 5,251,626 A | 10/1993 | Nickolls et al. |
| 5,267,560 A | 12/1993 | Cohen |
| 5,282,838 A | 2/1994 | Hauser et al. |
| 5,292,341 A | 3/1994 | Snell |
| 5,321,618 A | 6/1994 | Gessman |
| 5,372,607 A | 12/1994 | Stone et al. |
| 5,421,830 A | 6/1995 | Epstein et al. |
| 5,431,691 A | 7/1995 | Snell et al. |
| 5,456,691 A * | 10/1995 | Snell .............................. 607/30 |
| 5,456,952 A | 10/1995 | Garza et al. |
| 5,487,752 A | 1/1996 | Salo et al. |
| 5,507,782 A | 4/1996 | Kieval et al. |
| 5,540,727 A | 7/1996 | Tockman et al. |

(Continued)

FOREIGN PATENT DOCUMENTS

WO    WO-0041765    7/2000

(Continued)

OTHER PUBLICATIONS

Hall, Jeffrey A., et al., "Recordable Macros for Pacemaker Follow-Up", U.S. Appl. No. 10/348,191, filed Jan. 21, 2003, 17 pgs.

(Continued)

*Primary Examiner* — Mark W Bockelman
(74) *Attorney, Agent, or Firm* — Schwegman Lundberg & Woessner, P.A.

(57) ABSTRACT

A device and method for programming an implantable pulse generator. In one embodiment, commands are entered designating implantable pulse generator programming variables into programmer memory. At least some of the commands are transformed into an executable macro. The macro is stored in the programmer memory. The macro is executed to transmit the programming variables to the implantable pulse generator.

11 Claims, 3 Drawing Sheets

U.S. PATENT DOCUMENTS

| | | | |
|---|---|---|---|
| 5,549,654 A | 8/1996 | Powell | |
| 5,594,638 A | 1/1997 | Iliff | |
| 5,607,460 A | 3/1997 | Kroll et al. | |
| 5,630,835 A | 5/1997 | Brownlee | |
| 5,662,691 A | 9/1997 | Behan et al. | |
| 5,690,690 A * | 11/1997 | Nappholz et al. | 607/30 |
| 5,693,076 A | 12/1997 | Kaemmerer | |
| 5,716,382 A | 2/1998 | Snell | |
| 5,792,203 A | 8/1998 | Schroeppel | |
| 5,800,473 A | 9/1998 | Faisandier | |
| 5,833,623 A | 11/1998 | Mann et al. | |
| 5,891,178 A | 4/1999 | Mann et al. | |
| 5,911,132 A | 6/1999 | Sloane et al. | |
| 5,935,060 A * | 8/1999 | Iliff | 600/300 |
| 6,016,442 A | 1/2000 | Hsu et al. | |
| 6,070,101 A | 5/2000 | Struble et al. | |
| 6,073,049 A | 6/2000 | Alt et al. | |
| 6,091,990 A | 7/2000 | Hsu et al. | |
| 6,141,586 A | 10/2000 | Mower | |
| 6,148,234 A | 11/2000 | Struble | |
| 6,168,563 B1 | 1/2001 | Brown | |
| 6,249,705 B1 | 6/2001 | Snell | |
| 6,272,377 B1 | 8/2001 | Sweeney et al. | |
| 6,280,389 B1 | 8/2001 | Ding et al. | |
| 6,285,907 B1 | 9/2001 | Kramer et al. | |
| 6,304,773 B1 | 10/2001 | Taylor et al. | |
| 6,351,675 B1 | 2/2002 | Tholen et al. | |
| 6,370,427 B1 | 4/2002 | Alt et al. | |
| 6,400,982 B2 | 6/2002 | Sweeney et al. | |
| 6,411,847 B1 | 6/2002 | Mower | |
| 6,442,432 B2 | 8/2002 | Lee | |
| 6,442,433 B1 | 8/2002 | Linberg | |
| 6,497,655 B1 | 12/2002 | Linberg et al. | |
| 6,526,313 B2 | 2/2003 | Sweeney et al. | |
| RE38,119 E | 5/2003 | Mower | |
| 6,564,104 B2 | 5/2003 | Nelson et al. | |
| 6,622,040 B2 | 9/2003 | Ding et al. | |
| 6,625,494 B2 * | 9/2003 | Fang et al. | 607/48 |
| 6,668,194 B2 | 12/2003 | VanHout | |
| 6,669,631 B2 | 12/2003 | Norris et al. | |
| 6,999,815 B2 | 2/2006 | Ding et al. | |
| 7,003,349 B1 * | 2/2006 | Andersson et al. | 607/27 |
| 7,070,562 B2 | 7/2006 | Bardy | |
| 7,136,707 B2 | 11/2006 | Hall et al. | |
| 7,181,285 B2 | 2/2007 | Lindh et al. | |
| 7,899,534 B2 | 3/2011 | L et al. | |
| 2001/0031997 A1 | 10/2001 | Lee | |
| 2001/0039375 A1 | 11/2001 | Lee et al. | |
| 2002/0016550 A1 | 2/2002 | Sweeney et al. | |
| 2002/0120311 A1 | 8/2002 | Lindh et al. | |
| 2002/0123672 A1 | 9/2002 | Christophersom et al. | |
| 2003/0088290 A1 | 5/2003 | Spinelli et al. | |
| 2004/0122487 A1 | 6/2004 | Hatlestad et al. | |
| 2004/0133246 A1 | 7/2004 | Ding et al. | |
| 2004/0143304 A1 | 7/2004 | Hall et al. | |
| 2006/0116727 A1 | 6/2006 | Ding et al. | |
| 2007/0250125 A1 | 10/2007 | Lindh et al. | |
| 2011/0137368 A1 | 6/2011 | Lindh et al. | |

FOREIGN PATENT DOCUMENTS

| | | |
|---|---|---|
| WO | WO-0041766 | 7/2000 |

OTHER PUBLICATIONS

Lindh, Par, et al., "Expert System and Method", U.S. Appl. No. 09/748,791, filed Dec. 26, 2000, 45 pgs.

Mower, Morton, U.S. Appl. No. 10/214,474, filed Aug. 8, 2002, entitled "Method and Apparatus for Treating Hemodynamic Disfunction", 3.

"U.S. Appl. No. 11/624,035, Notice of Allowance mailed Oct. 25, 2010", 9 pgs.

"U.S. Appl. No. 13/027,681, Non Final Office Action mailed May 26, 2011", 8 pgs.

"U.S. Appl. No. 13/027,681, Non-Final Office Action mailed May 26, 2011", 8 pgs.

"U.S. Appl. No. 13/027,681, Notice of Allowance mailed Sep. 22, 2011", 6 pgs.

"U.S. Appl. No. 13/027,681, Response filed Aug. 26, 2011 to Non-Final Office Action mailed May 26, 2011", 13 pgs.

"U.S. Appl. No. 09/748,791, Advisory Action mailed Aug. 4, 2004", 3 pgs.

"U.S. Appl. No. 09/748,791, Final Office Action mailed Mar. 9, 2004", 6 pgs.

"U.S. Appl. No. 09/748,791, Final Office Action mailed Aug. 23, 2005", 6 pgs.

"U.S. Appl. No. 09/748,791, Non Final Office Action mailed Feb. 21, 2003", 9 pgs.

"U.S. Appl. No. 09/748,791, Non Final Office Action mailed Sep. 17, 2003", 8 pgs.

"U.S. Appl. No. 09/748,791, Notice of Allowance mailed Sep. 20, 2006", 5 pgs.

"U.S. Appl. No. 09/748,791, Preliminary Amendment filed Feb. 21, 2001", 2 pgs.

"U.S. Appl. No. 09/748,791, Response filed May 10, 2006 to Non Final Office Action mailed Feb. 10, 2006", 8 pgs.

"U.S. Appl. No. 09/748,791, Response filed Jul. 5, 2005 to Non Final Office Action mailed Feb. 3, 2005", 7 pgs.

"U.S. Appl. No. 09/748,791, Response filed Jul. 9, 2004 to Final Office Action mailed Mar. 9, 2004", 11 pgs.

"U.S. Appl. No. 09/748,791, Response filed Jul. 21, 2003 to Non Final Office Action mailed Feb. 21, 2003", 15 pgs.

"U.S. Appl. No. 09/748,791, Response filed Nov. 23, 2005 to Final Office Action mailed Aug. 23, 2005", 7 pgs.

"U.S. Appl. No. 09/748,791, Response filed Nov. 25, 2002 to Non Final Office Action mailed Aug. 28, 2002", 7 pgs.

"U.S. Appl. No. 09/748,791, Response filed Dec. 17, 2003 to Non Final Office Action mailed Sep. 17, 2003", 10 pgs.

"U.S. Appl. No. 09/748,791, Non Final Office Action mailed Feb. 3, 2005", 6 pgs.

"U.S. Appl. No. 09/748,791, Non Final Office Action mailed Feb. 10, 2006", 9 pgs.

"U.S. Appl. No. 09/748,791, Non-Final Office Action mailed Aug. 28, 2002", 7 pgs.

"U.S. Appl. No. 09/748,791, Notice of Allowance mailed mailed Sep. 3, 2004", 7 pgs.

US 6,527,714, 03/2003, Bardy (withdrawn)

* cited by examiner

RECORDABLE MACROS FOR PACEMAKER FOLLOW-UP

PRIORITY

This application is a Division of U.S. application Ser. No. 10/348,191, filed on Jan. 21, 2003, now issued as U.S. Pat. No. 7,136,707, which is incorporated herein by reference.

FIELD OF THE INVENTION

This document relates to systems implantable in a patient to treat cardiac arrhythmia, and in particular, to a programming device and method for using software or firmware macro-functions (hereinafter macros) to record a physician's programming preferences and procedural test order to partly automate follow-up procedures after a pacemaker, defibrillator, or any other device capable of diagnosing and treating cardiac arrhythmia has been implanted in a patient.

BACKGROUND

External programmers are used to non-invasively change the performance parameters of an implanted device such as a pacemaker or defibrillator. As the implantable devices become more sophisticated and are designed with more programmable features, it is advantageous to reduce the time necessary for physicians to change programming preferences for the implanted devices. Current methods require the operator of a programmer for an implanted device to re-enter a set of programmed parameters for the implanted device at the start of a follow-up procedure. This set of parameters may be defined by physician preferences or by settings needed to perform a test. The re-entry of programmed settings results in extra time needed to program the implanted device to overwrite default settings or perform a set of tests. What is needed is a programming device and method to automatically pre-load the set of parameters in the programming device to minimize the time necessary to reprogram the settings of the implanted device.

SUMMARY OF THE INVENTION

This document discusses a device and method for programming an implantable pulse generator. The programming device for an implantable pulse generator comprises a programmer memory, data entry means to enter implantable pulse generator programming variables into the programmer memory, a processor to transform the entry of programming variables into an executable macro as the variables are entered and storing the macro in the programmer memory, and a communication module to transmit the programming variables to the pulse generator when the processor executes the macro.

One embodiment of a method of programming an implantable pulse generator comprises entering commands designating implantable pulse generator programming variables into programmer memory, transforming at least some of the commands into an executable macro, storing the macro in the programmer memory, and executing the macro to transmit the programming variables to the implantable pulse generator. Another embodiment of a method of programming an implantable pulse generator comprises receiving data identifying the implantable pulse generator by an external programming device, loading a script file previously stored according to the identifying data into memory of the programming device, executing the script file to pre-load programming variables into the memory of a programming device, and selectively transmitting the programming variables via telemetry from the programming device to the implantable pulse generator for storage in memory of the implantable pulse generator.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, where like numerals refer to like components throughout the several views.

DETAILED DESCRIPTION

In the following detailed description, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Figure 1:
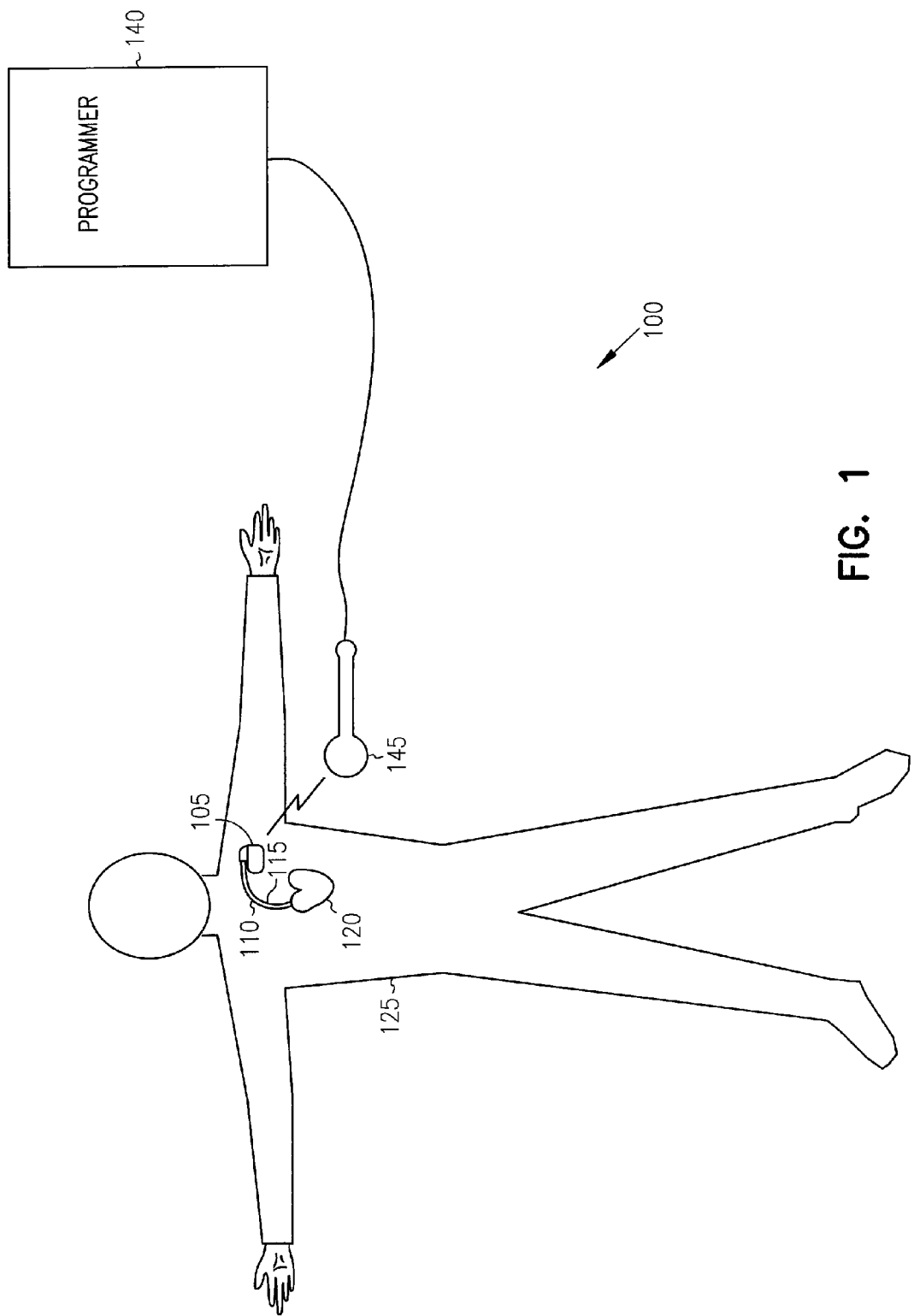
FIG. 1 shows one embodiment of a system to treat cardiac arrhythmia and an environment in which it is used.

FIG. 1 shows one embodiment of portions of a system 100 to treat cardiac arrhythmia. System 100 includes an implantable pulse generator (PG) 105 that is connected by a first cardiac lead 110 and a second cardiac lead 115, or one or more additional leads, to a heart 120 of a patient 125. Implantable PG 105 can take the form of a pacemaker, a defibrillator, or a cardioverter/defibrillator that includes pacing capability. System 100 also includes an external programming device, or programmer, 140 that provides for wireless communication with the implantable PG 105 using telemetry antenna 145. The external programmer transmits the programming variables to the implantable PG. The programming variables determine what therapy will be used to treat heart arrhythmias. The external programmer also receives information such as device serial numbers from the implantable PG 105.

Figure 2:
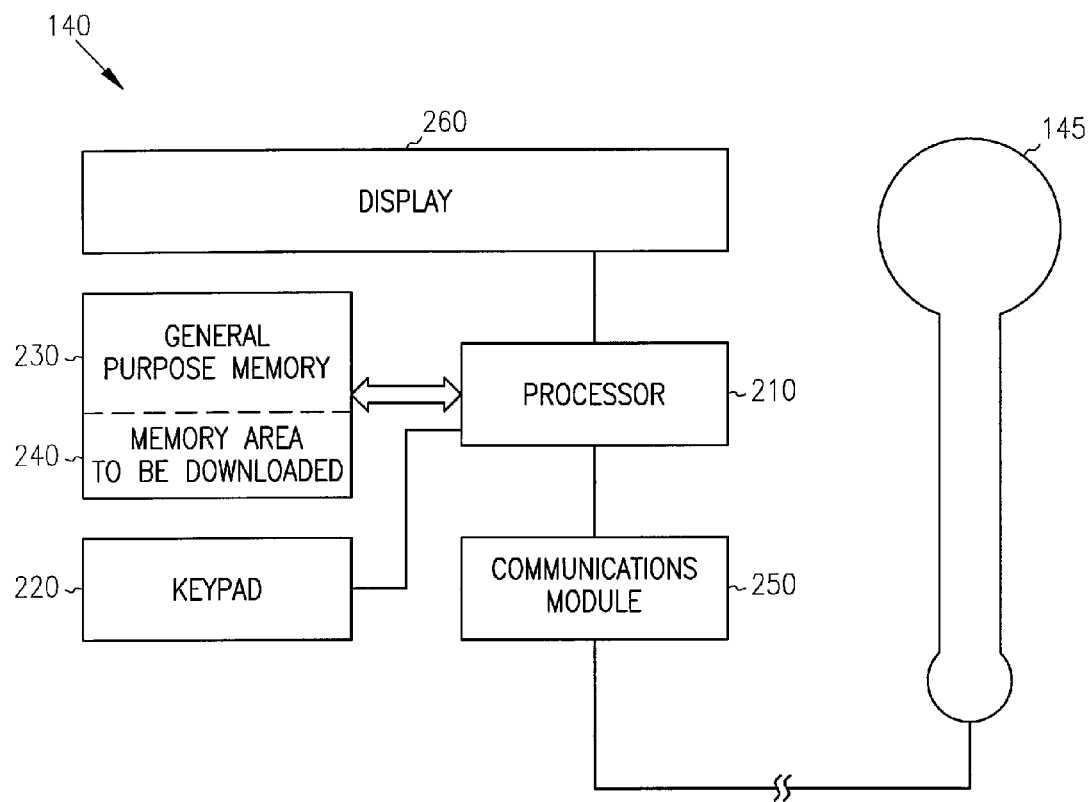
FIG. 2 is a block diagram of the components of an external programming device for an implantable device.

FIG. 2 is a block diagram of a programmer 140 for the implanted device. An operator enters programming variables by data entry means 220 into a memory 240 local to the external programmer 140 for transmitting to an implantable PG 105. The programming variables are shown to the operator by programmer display 260. In one embodiment, data entry means 220 is a keypad. In another embodiment, data entry means 220 is a computer mouse. In a further embodiment, the data entry means 220 is a drop-down menu and a computer mouse or a touch-screen display. In a further embodiment, data entry means 220 is a virtual keyboard which may be part of the programmer display 260. Processor 210 transforms the data entries of an operator into general memory 230 as a software or firmware macro. In one embodiment, memory 230 is a local hard drive for the programmer. In another embodiment, memory 230 is a diskette inserted into a local floppy disk drive. In an embodiment concerning the software of the programmer, the processor runs a software program such as VisualBasic™ (for a MS Windows based programmer) or QNX™ programming script (for QNX based programmers), or a program residing in firmware to record the macro.

The programmer then transmits the programming variables to the implantable PG 105 using communication module 250 and telemetry antenna 145. In one embodiment, the set of programming variables to be transmitted to the implantable PG 105 is defined by the device feature set of the type of implantable device. In another embodiment, the set of programming variables is defined by the cardiac disorder that afflicts the patient. In a further embodiment, the set of programming variables to be transmitted to the implantable PG 105 is checked to prevent overwriting a protected area of memory in the implanted device. In yet a further embodiment, the set of programming variables re-entered for downloading to the implantable PG 105 is checked to determine if the variable is appropriate for the implanted system. For example, the operator may try to download a pacing parameter for a pacing vector that is not implemented in the device. In subsequent programming sessions, processor 210 plays back the macro to either directly transmit the variables to the PG 105, or to pre-load the programming variables into local programmer memory 240 before selectively transmitting the variables to the PG 105.

Figure 3:
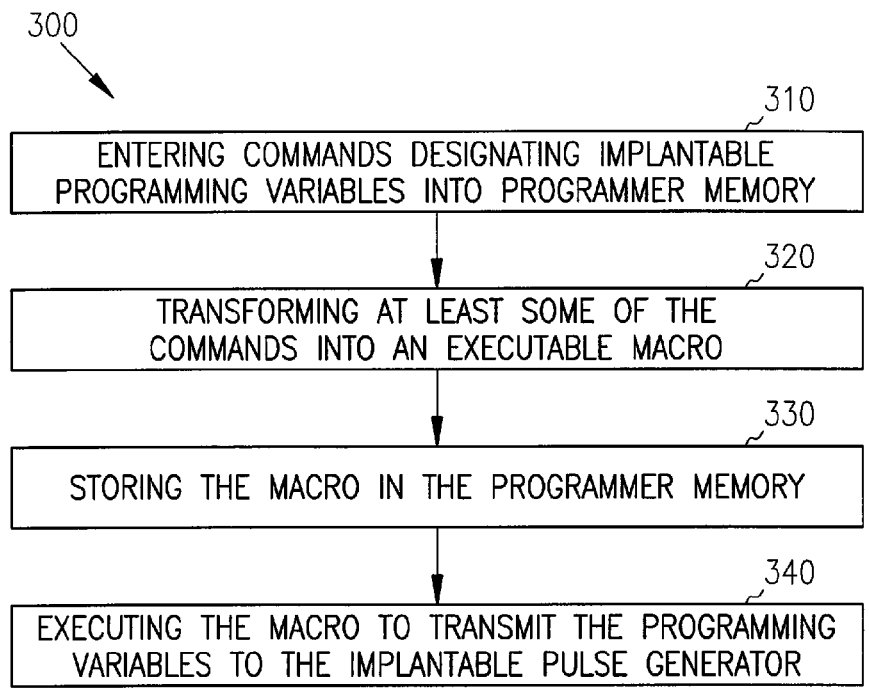
FIG. 3 is a flow chart showing one embodiment of a method of programming an implantable device using macros.

FIG. 3 is a flow chart showing one embodiment of a method 300 of programming an implanted device using macros. At 310 commands are entered designating implantable programmer variables into programmer memory. In one example of the embodiment, commands are entered by a programmer operator using a keypad. In another embodiment, a programmer operator enters programming variables into fields of the display 260. At 320 at least some of the commands are transformed into an executable macro. In one embodiment, commands are transformed by processor 210 recording the keystrokes of a programmer operator when the operator enters commands using a keypad. In another embodiment, the processor records a series of data values entered into fields of display 260. At 330, the executable macro is stored into programmer memory 230. At 340, the macro is executed to transmit the programming variables to the implantable PG 105.

In one embodiment, the macro pre-loads physician setting preferences to overwrite the default factory settings; especially in the area of electrophysiological testing, anti-tachycardia pacing (ATP), and other programmed stimulation.

In another embodiment, data identifying the implantable PG 105, such as the device serial number for example, is uploaded from the implantable PG 105, and the macro pre-loads variables required to conduct patient-testing of the device. In this manner, an entire set of tests is pre-programmed by replaying macros. The test results and programmed parameters are extracted from the external programmer 140 and inserted into a post-session follow-up communication. One embodiment of the communication is a predefined physician follow-up letter using, for example, additional macros written in Visual Basic™ for use in a word processing program such as MS Word™. Often a transfer of information between two different operating systems (OS) such as QNX™ (OS for the programmer) and MS Windows™ (OS for the computer generating physician follow-up letters) is performed through creation of a diskette with appropriate ANSI values to be imported into the word processing program such as MS Word™ or Word Perfect™.

Figure 4:
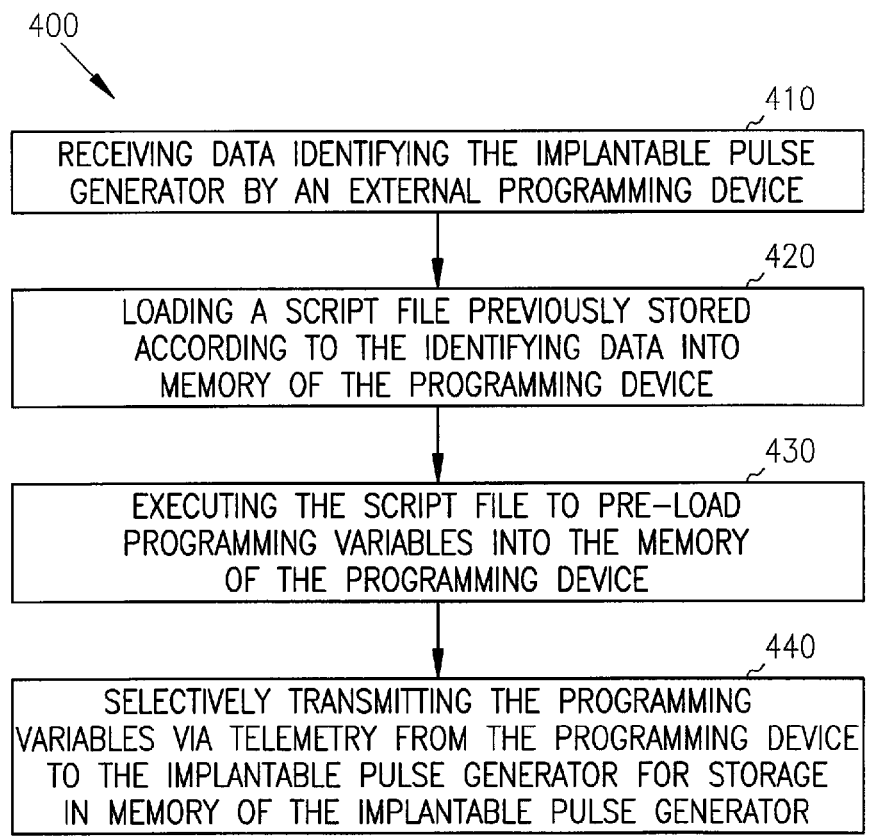
FIG. 4 is a flow chart showing one embodiment of a method of programming an implantable device using a previously stored script file.

FIG. 4 is a flow chart showing one embodiment of a method 400 of programming an implanted device using a previously stored script file. A script file is a text file written in a software language such as Visual Basic™ containing a sequence of executable commands. At step 410 the external programming device 140 receives data identifying the implantable PG 105. At step 420, the programming device 140 then loads a script file previously stored according to the identifying data into memory 230 of the programming device 140. In one embodiment, the programming device 140 displays a menu of script files associated with the implantable PG 105. In one example of associating the menus with the implantable PG 105, the menu displays the script files available for the model of PG 105. In another example, the menu displays the script files available for the cardiac disorder treated with the PG 105. In a further example, the menu displays the script files available for different cardiac disorders that require specific device programming of the PG 105.

In another embodiment, the script file menus are associated with the device programming preferences of a physician. In one example, the script file menus are associated with a physician's preferences for the model of the PG 105. In another example, the script file menus are associated with a physician's preferences for a set of tests to execute based on the cardiac disorder. At step 430, the script file chosen by the operator from a menu is executed to pre-load programming variables into local memory 240 of programming device 140. At step 440, the programming variables are selectively transmitted via telemetry from the programming device 140 to the implantable pulse generator for storage in memory of the implantable PG 105. In one embodiment of selectively transmitting the programming variables, the script file either transmits the variables via telemetry to the PG 105 by the operator without modification, or the variables are transmitted after review and minor changes are made by the operator.

Although specific examples have been illustrated and described herein, it will be appreciated by those of ordinary skill in the art that any other embodiment that exists that is calculated to achieve the same purpose may be substituted for the specific example shown. This application is intended to cover any adaptations or variations of the present invention. Therefore, it is intended that this invention be limited only by the claims and their equivalents.

What is claimed is:

1. A method of programming an implantable pulse generator, the method comprising:
receiving data identifying the implantable pulse generator by an external programming device;
loading a script file previously stored according to the identifying data into memory of the programming device, wherein loading a script file includes presenting a script file according to a cardiac disorder in which modification of at least one programming parameter of the implantable pulse generator is needed to treat the cardiac disorder;
executing the script file to:
pre-load programming variables into the memory of a programming device; and
present at least a portion of the programming variables on a display for modification, if any, by an operator;
checking any modified programming variables to determine if the modification is appropriate for the implantable pulse generator; and
selectively transmitting the programming variables via telemetry from the programming device to the implantable pulse generator for storage in memory of the implantable pulse generator.

2. The method of claim 1, wherein loading a script file includes loading at least one previously stored script file corresponding to the data identifying the implantable pulse generator.

3. The method of claim 1, wherein loading a script file includes loading at least one previously stored script file corresponding to a model type of the implantable pulse generator.

4. The method of claim 1, wherein loading a script file includes loading at least one previously stored script file corresponding to a cardiac disorder of a patient.

5. The method of claim 1, wherein loading a script file includes loading a script file particularized to programmable features of the implantable pulse generator.

6. The method of claim 1, wherein loading a script file includes loading a script file corresponding to a physician's preferences for pulse generator programming variables.

7. The method of claim 6, wherein loading a script file includes loading a script file corresponding to preferences of a physician for an implantable pulse generator model.

8. The method of claim 6, wherein loading a script file includes loading a script file corresponding to preferences of a physician for a cardiac disorder.

9. The method of claim 1, wherein loading a script file includes loading a script file corresponding to one of a plurality of tests to be performed.

10. The method of claim 1, wherein loading a script file includes loading a script file containing a plurality of tests ordered according to a physician's preference.

11. The method of claim 1, wherein the method further includes extracting the order of the plurality of tests and the test results from the programmer for insertion into a post-session follow-up communication.

* * * * *